(12) United States Patent
Falligant et al.

(10) Patent No.: US 6,585,016 B1
(45) Date of Patent: Jul. 1, 2003

(54) KEYED ANESTHETIC VAPORIZER FILLING SYSTEM

(75) Inventors: John C. Falligant, Edgerton, WI (US); Gordon G. Sansom, Sun Prairie, WI (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 10/099,647

(22) Filed: Mar. 15, 2002

(51) Int. Cl.[7] ................................................ B65B 1/04
(52) U.S. Cl. ...................... 141/352; 141/18; 141/354; 141/364; 141/366; 128/202.22; 128/202.27; 128/203.12
(58) Field of Search ........................... 141/18, 21, 346, 141/351–354, 363–366; 128/202.22, 202.27, 203.12

(56) References Cited

U.S. PATENT DOCUMENTS

| | | | |
|---|---|---|---|
| 1,600,549 A | 9/1926 | Jurs | |
| 2,202,459 A | 5/1940 | Link | 221/84 |
| 3,115,907 A | 12/1963 | Labat | 141/295 |
| 3,125,135 A | 3/1964 | Boyer et al. | 141/290 |
| 3,146,808 A | 9/1964 | Zellweger | 141/293 |
| 3,217,762 A | 11/1965 | Burchett | 141/349 |
| 3,277,674 A | 10/1966 | Klein et al. | 67/7.1 |
| 3,416,577 A | 12/1968 | Franz | 141/117 |
| 3,799,222 A | 3/1974 | Franz | 141/291 |
| 3,874,380 A | 4/1975 | Baum | 128/206 |
| 4,614,437 A | 9/1986 | Buehler | 366/130 |
| 4,883,049 A | 11/1989 | McDonald | 128/202.22 |
| 4,893,659 A | 1/1990 | Loliger | 141/85 |
| 5,170,823 A | 12/1992 | Gregory et al. | 141/382 |
| 5,287,898 A | 2/1994 | Falb et al. | 141/329 |
| 5,381,836 A | 1/1995 | Braatz et al. | 141/21 |
| 5,505,236 A | 4/1996 | Grabenkort et al. | 141/329 |
| 5,617,906 A | 4/1997 | Braatz et al. | 141/21 |
| 5,758,640 A | * 6/1998 | Kamppari et al. | 128/202.27 |
| 5,911,250 A | * 6/1999 | Turker et al. | 141/94 |
| 5,915,427 A | * 6/1999 | Grabenkort | 141/364 |

FOREIGN PATENT DOCUMENTS

| | | |
|---|---|---|
| DE | 1900271 | 1/1969 |
| DE | 4106756 | 3/1991 |
| FR | 2161201 | 2/1975 |
| WO | WO 92/12752 | 8/1992 |
| WO | WO 93/09753 | 5/1993 |

* cited by examiner

*Primary Examiner*—J. Casimer Jacyna
(74) *Attorney, Agent, or Firm*—Andrus, Sceales, Starke & Sawall, LLP

(57) ABSTRACT

A system for facilitating the delivery of a liquid anesthetic agent from an anesthetic bottle to an anesthetic vaporizer. The system includes a bottle adapter, an anesthetic bottle and a filler arrangement positioned on the anesthetic vaporizer. The bottle adapter and filler arrangement each include a keyed configuration such that only the correct type of anesthetic agent can be emptied into the anesthetic vaporizer. The bottle adapter includes an adapter valve assembly that engages a filler valve assembly contained within the filler. The dimensions and arrangement of the adapter valve assembly and the filler valve assembly insure anesthetic agent is delivered to the anesthetic vaporizer only when the anesthetic agent can safely flow from the anesthetic bottle to the anesthetic vaporizer.

46 Claims, 12 Drawing Sheets

KEYED ANESTHETIC VAPORIZER FILLING SYSTEM

BACKGROUND OF THE INVENTION

The present invention generally relates to a system for transferring a liquid anesthetic agent from an anesthetic bottle to an anesthetic vaporizer. More specifically, the present invention relates to an anesthetic vaporizer filling system that includes a unique valve arrangement and keyed engagement system that prevents the anesthetic agent from being released to atmosphere during filling and insures that only the desired type of anesthetic agent can be discharged into the anesthetic vaporizer.

Anesthetic agents are typically volatile substances with relatively low boiling points and high vapor pressures. Anesthetic agents can be flammable and explosive in both their liquid and vapor states. Further, inhalation of vapor by healthcare personnel in the area near where the anesthetic agent is being used can cause drowsiness. An anesthetic agent is administered to a patient during anesthesia by means of an anesthetic vaporizer. The agent is supplied to the patient from an internal sump within the vaporizer as a vapor, while the agent is stored within the sump as a liquid. The anesthetic agent is typically mixed with oxygen and nitrous oxide prior to its delivery to the patient for inhalation.

Devices and filling systems have been designed for the transfer of the anesthetic agent from a supply container, such as an anesthetic bottle, to the vaporizer sump through a closed system that minimizes the escape of anesthetic gas to the atmosphere. These devices are designed so that during set-up and disassembly procedures, the anesthetic bottle is not open and exposed to atmosphere.

One example of such a system is shown in the Grabenkort U.S. Pat. No. 5,505,236. In this patent, the filling system lacks implementation of a filler probe seal, which in turn forces the implementation of a fill vent. The fill vent is required to prevent increased vapor pressure within the sump and filling system from causing egress of anesthetic agent between the filler probe (bottle) and filler receiver (vaporizer). As a result, the fill vent allows release of anesthetic vapor to atmosphere during the filling process (most notably when filling a vaporizer with dry sump and wick). Further, the anesthetic bottle includes a plunger that is biased by a first spring. When the anesthetic bottle is pressed into the filler of the anesthetic vaporizer, the plunger contacts the outer surface of an inlet valve member that in turn is biased to a closed position by a second spring. The first and second springs are configured such that the second spring holding the inlet valve member is weaker than the first spring biasing the plunger in the anesthetic bottle. This configuration of springs insures that the inlet valve member opens prior to anesthetic agent leaving the anesthetic bottle. Therefore, the relative spring strengths of the pair of springs in the Grabenkort reference are critical to insure that the anesthetic agent is not released to atmosphere. If the strength of either spring changes after repeated use, or if one of the springs is not properly calibrated, anesthetic vapor could be released to atmosphere. This system, therefore, has several drawbacks that need to be addressed.

Presently, many types of anesthetic agents are available for use during anesthesia. These anesthetic agents include, but are not limited, to: Enflurane, Halothane, Isoflurane and Sevoflurane. Each of these anesthetic agents has different properties and vaporizers are typically designed to deliver the anesthetic agents differently depending upon the properties of the anesthetic agent. Therefore, it is important that only the correct type of anesthetic agent is delivered to the vaporizer.

Currently, the International Standardization Organization (ISO) has developed standard 5360:1993 that mandates the inclusion of a pair of protrusions on an anesthetic agent bottle. The standard calls for a specific angle between the protrusions around the bottle that is based upon the type of anesthetic agent contained within the anesthetic bottle. Because the anesthetic container for each type of anesthetic agent has its own set of protrusions and color, and because a corresponding connector device for the anesthetic bottle fits only the type of vaporizer designed for that type of anesthetic, the probability of inadvertently using the wrong type of anesthetic in a vaporizer has been greatly reduced.

Although the anesthetic bottle may include protrusions specifically positioned based on the type of anesthetic contained within the bottle and can be emptied by keyed connector tubes, typical anesthetic bottles do not include a valve arrangement that can be used to prevent loss of the anesthetic agent to atmosphere during filling. Further, the keyed connector tubes are of a small size which reduce the rate of filling the vaporizer, and require manual operation of mechanisms to retain the keyed tubes in the vaporizer while filling, and to operate valving in the vaporizer to receive the anesthetic from the keyed connector tubes. Further, the keyed connector tubes themselves contain no valving to prevent loss of anesthetic vapor from the bottle when the bottle is not connected to the vaporizer, or the loss of liquid from the bottle if the bottle is inverted while not connected to the vaporizer. Further, due to the horizontal nature of the receiving ports in vaporizers for such keyed connector tubes, small amounts of liquid anesthetic persist in the tubing when the keyed connector tubes are disconnected from the vaporizer. This liquid anesthetic is then lost, since it is not retained either in the vaporizer or the keyed connector tubes.

Therefore, a need exists for an anesthetic vaporizer filling system that allows a bottle adapter having a unique valve assembly to be attached to the anesthetic bottle. Further, a need exists for a system having a specifically configured filling station that interacts with the bottle adapter to insure that the anesthetic agent is not released to atmosphere during the filling procedure. Further, a need exists for the filling station of the anesthetic vaporizer to have a unique configuration that receives only a specified type of anesthetic agent.

SUMMARY OF THE INVENTION

The present invention relates to a filling system for use in the delivery of a liquid anesthetic agent from an anesthetic bottle to the internal sump of an anesthetic vaporizer. The filling system includes a keyed registration system such that only the desired type of anesthetic agent can be dispensed into a particular anesthetic vaporizer. Further, the filling system of the present invention minimizes the amount of anesthetic agent released to atmosphere during the filling sequence.

The anesthetic vaporizer filling system of the present invention includes a bottle adapter that is configured for attachment to an anesthetic bottle. The bottle adapter includes internal threads that are configured to receive the threaded neck of the anesthetic bottle in conformance with the ISO 5360:1993 standard. The bottle adapter includes a pair of receiving slots positioned around its outer circumference that receive protrusions formed on the anesthetic bottle in conformance with the ISO 5360:1993 standard. The receiving slots insure that each bottle adapter is attachable only to a single, specific type of anesthetic agent.

The bottle adapter of the present invention is formed from nylon and colored in accordance with the ISO standard colors for anesthetic agents, in conformance with the ISO 5360:1993 standard. The color of the bottle adapter, and matching colored features adjacent to the filler on the vaporizer, such as covers and labels, further insure that the proper type of anesthetic agent is being delivered.

The bottle adapter includes a keyed section used to insure that only a single, correct bottle adapter can be used with an anesthetic vaporizer. The keyed section includes a pair of indexing ridges formed along its outer circumference. The first indexing ridge is located at a home position and the second indexing ridge is spaced from the first indexing ridge around the outer circumference of the keyed section by an angle $\alpha$. The angle $\alpha$ is related to the type of anesthetic agent to which the bottle adapter will be applied. In the preferred embodiment of the invention, the angle $\alpha$ between the pair of indexing ridges is the same as the angle between the protrusions on the anesthetic bottles, as determined by the ISO standard.

The bottle adapter includes an adapter valve assembly that is positioned within the interior of the bottle adapter. The adapter valve assembly is movable between an open position and a closed position to regulate the flow of anesthetic agent from the anesthetic bottle to which the bottle adapter is mounted. Specifically, the adapter valve assembly includes an elongated valve stem having a valve head formed on one end. The valve head includes a conical sealing surface that engages a corresponding sealing seat formed on an annular flange extending into the interior of the bottle adapter. The valve head is biased into a closed position by a spring.

The outer diameter of the bottle adapter includes a probe section. The probe section is joined to the keyed section. The probe section is defined at its outer edge by a top lip. The top lip is used to position a sealing ring surrounding the outer circumference of the probe section.

The bottle adapter of the filling system of the present invention is sized to mate with a filling station mounted to the anesthetic vaporizer. The filling station is configured to receive only one type of bottle adapter to insure that the proper anesthetic agent is delivered to the anesthetic vaporizer.

The filling station includes a filler body that is secured to a mounting block of the anesthetic vaporizer. The filler body defines an open interior that is in communication with an internal cavity formed in the mounting block. The internal cavity drains to the sump of the anesthetic vaporizer such that the anesthetic agent can be directed to the sump.

The body of the filling station includes a filler spout formed on its outer end. The filler spout includes a cylindrical outer wall having a series of indexing grooves formed therein. The indexing grooves formed on the outer wall of the filler spout are positioned at an angle relative to each other around the circumference of the filler spout. The angle between the indexing grooves is based upon the ISO standard and the type of anesthetic agent to be discharged into the anesthetic vaporizer including the filling station. Preferably, the indexing grooves each includes a recessed top edge surface that allows a user of the anesthetic vaporizer to quickly identify the position of the indexing grooves on the filling station.

The filling station includes a filler valve assembly that is movable between an open position and a closed position. When the filler valve assembly is in the closed position, anesthetic agent is prevented from draining into the internal sump of the anesthetic vaporizer which prevents the wrong anesthetic agent being poured into the vaporizer from an open bottle without the presence of a correct bottle adapter.

In accordance with one aspect of the invention, the filler valve assembly includes a valve body having a conical sealing surface. The conical sealing surface is biased into contact with a seal formed near the bottom edge of the filler body. The interaction between the conical sealing surface of the valve body and the seal provides a liquid-tight seal to prevent anesthetic agent from inadvertently being dispensed into the anesthetic vaporizer.

The filler valve assembly further includes a centrally located stationary activation rod that is immovably located within the filler body, along the centerline of the filling station. The activation rod is secured to a mounting block, which in turn is mounted to the inner surface of the filler body. The mounting block includes a series of cylindrical openings that allow anesthetic agent to flow past the otherwise solid mounting block.

The valve body of the filler valve assembly includes a plurality of projecting legs that each extend through one of the cylindrical openings formed in the mounting block. In this manner, the valve body extends past the stationary mounting block such that the protruding legs and valve body are movable relative to the stationary mounting block and stationary fixed activation rod.

A bias spring is positioned to urge the valve body into contact with the seal to prevent inadvertent filling of the anesthetic vaporizer with a supply of anesthetic agent. As described, the implementation of the fixed activation rod eliminates the dependency on relative spring rates between the movable valve body of the vaporizer and the adapter valve assembly of the bottle adapter.

In accordance with the present invention, the filling system allows the bottle adapter to be securely coupled to the filling station as follows. Initially, the bottle adapter is attached to the correct type of anesthetic bottle. The interaction between the mounting slots formed in the bottle adapter and the protrusions on the anesthetic agent bottle insure that the bottle adapter is used upon only the correct type of anesthetic agent.

Once the bottle adapter has been installed, the bottle adapter is brought into engagement with the filling station. As the bottle adapter is inserted into the filling station, the indexing ridges on the bottle adapter are brought into engagement with the indexing grooves formed in the filling station. If the indexing grooves and indexing ridges match, the bottle adapter can be fully inserted into the filling station as will be described. However, if the indexing grooves do not match the indexing notches, the bottle adapter is prevented from fully entering into the filling station.

If the bottle adapter is correct for the anesthetic vaporizer, the bottle adapter is inserted further into the filling station. As the bottle adapter is inserted, the sealing ring formed around the probe section of the bottle adapter engages a smooth inner surface formed within the filler body of the filling station. The interaction between the sealing ring and the smooth inner surface provides a gas-tight seal to prevent built-up gas within the anesthetic vaporizer from being released to atmosphere.

As the bottle adapter is moved further into engagement with the filling station, the top lip of the bottle adapter contacts the projecting legs formed on the valve body of the filler valve assembly. Slightly further movement of the bottle adapter causes the bottle adapter to move the valve body away from the seal and open the filler valve assembly.

In another aspect of the invention, the dimensions of the bottle adapter and filling station are selected such that when the bottle adapter initially opens the filler valve assembly, the top end of the stationary activation rod is spaced slightly from a recessed face surface formed on the valve head of the adapter valve assembly. Thus, the filler valve assembly opens prior to opening of the adapter valve assembly.

Further movement of the bottle adapter into the filling station results in the stationary activation rod moving the valve head of the adapter valve assembly to an open position. When in the open position, anesthetic agent can flow through the bottle adapter and into the filling station.

As can be understood by the above description, the sealing ring formed around the bottle adapter provides for a gas seal prior to opening of either the adapter valve assembly or the filler valve assembly. Additionally, the interaction between the keyed section of the bottle adapter and the filler spout of the filling station insure the proper type of anesthetic agent is being dispensed prior to opening of either valve assembly within the filling system If the correct bottle adapter is being used, the invention insures that the filler valve assembly opens prior to the adapter valve assembly such that any discharged anesthetic agent is able to flow into the anesthetic vaporizer.

In accordance with yet another aspect of the present invention, the stationary activation rod can include an internal passageway having a first opening and a second opening. The first and second openings of the activation rod are positioned on opposite sides of the seal created by the valve body. This establishes a vent path to the sump for draining of anesthetic agent from the vaporizer such that with the drain plug opened, and the filler cap loosened, venting of the sump is accomplished, facilitating drainage.

In another aspect of the invention, the anesthetic vaporizer can include a colored indicator mark, label, feature or cover near the filling station that indicates the type of anesthetic agent to be dispensed into the vaporizer. The color of the indicating mark on the anesthetic vaporizer directly corresponds to the color of the bottle adapter to be used with the correct type of anesthetic agent. The positioning of such colored marks, features or components directly adjacent to the filler is chosen to present to the operator a direct color contrast with the bottle adapter in the event that the incorrect adapter is offered up to the vaporizer filler.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings.

DETAILED DESCRIPTION OF THE INVENTION

Figure 1:
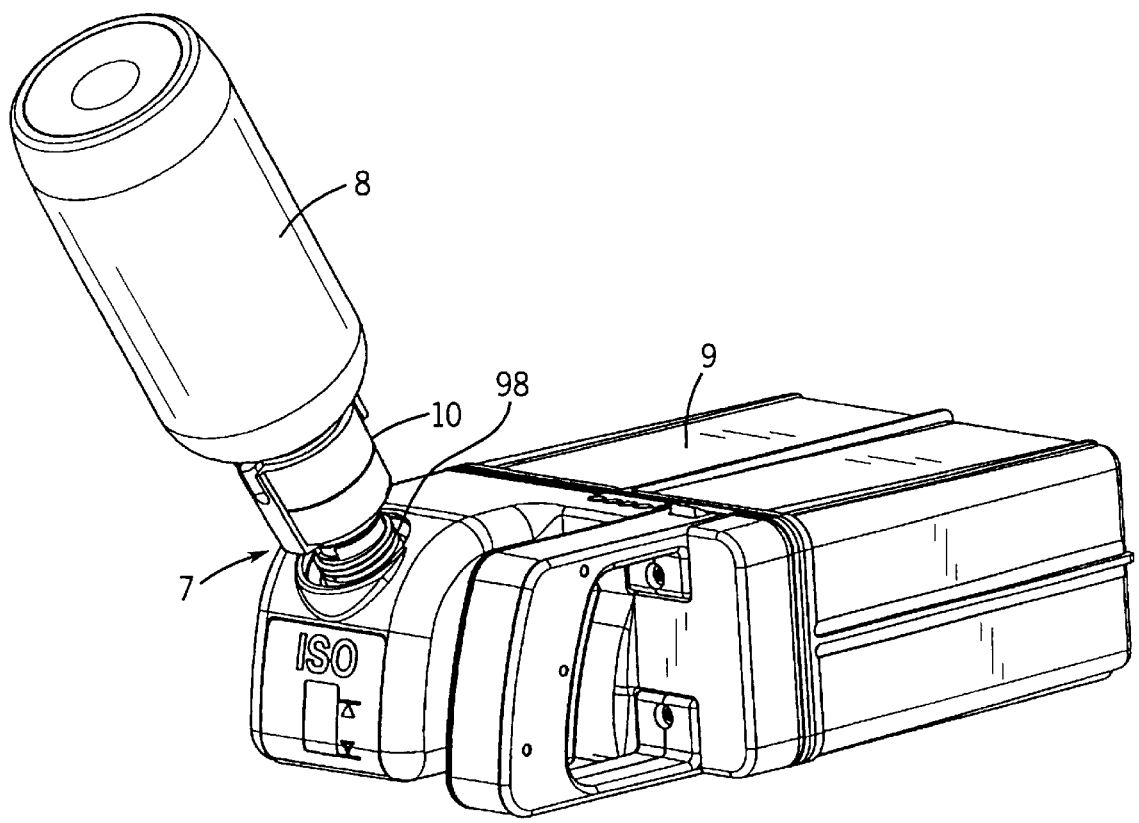
FIG. 1 is a perspective view illustrating an anesthetic vaporizer filling system of the present invention as used with an anesthetic vaporizer.

Referring first to FIG. 1, the present invention relates to an anesthetic vaporizer filling system 7 for connecting an anesthetic bottle 8 to a vaporizer 9 for filling the internal sump within the vaporizer 9 with anesthetic agent contained within the anesthetic bottle 8. The drawings and description of the present invention illustrate the filling system used to accomplish this function. For ease of understanding, the features of the anesthetic bottle 8 and the actual anesthetic vaporizer 9 are not shown in the figures, since these two components are available in many types of configurations and do not form part of the present invention.

FIGS. 1–8 illustrate a bottle adapter 10 that forms part of the anesthetic vaporizer filling system of the present invention. The bottle adapter 10 is configured for attachment to the anesthetic bottle 8 that includes ISO 5360:1993 agent-specific features. The bottle adapter 10 can be attached and removed from the anesthetic bottle 8 such that the anesthetic vaporizer filling system of the present invention can be utilized repeatedly with anesthetic bottles.

Figure 2:
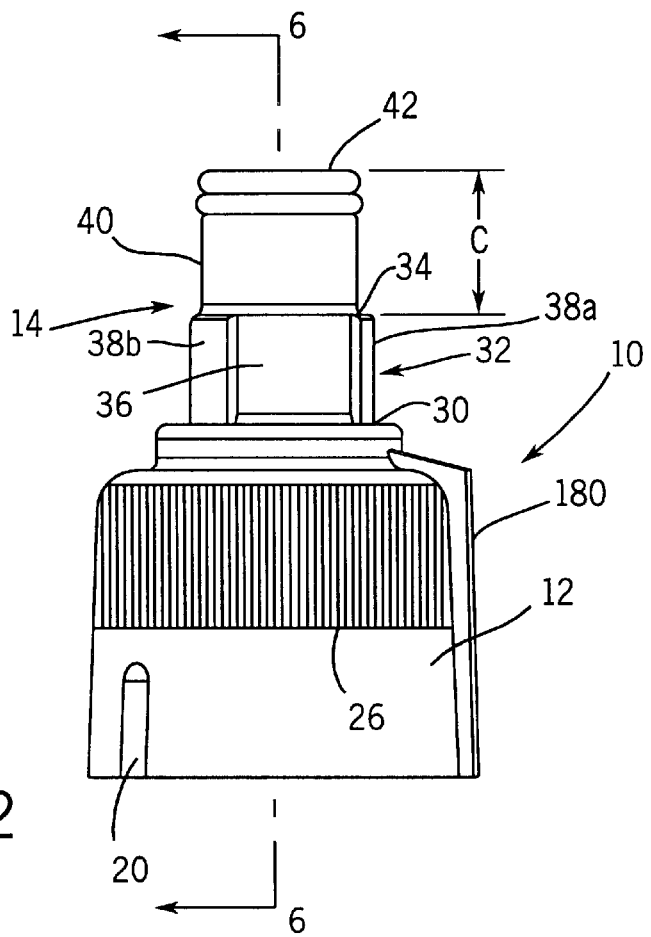
FIG. 2 is a side view of a bottle adapter for use in the anesthetic vaporizer filling system of the present invention.
Figure 6:
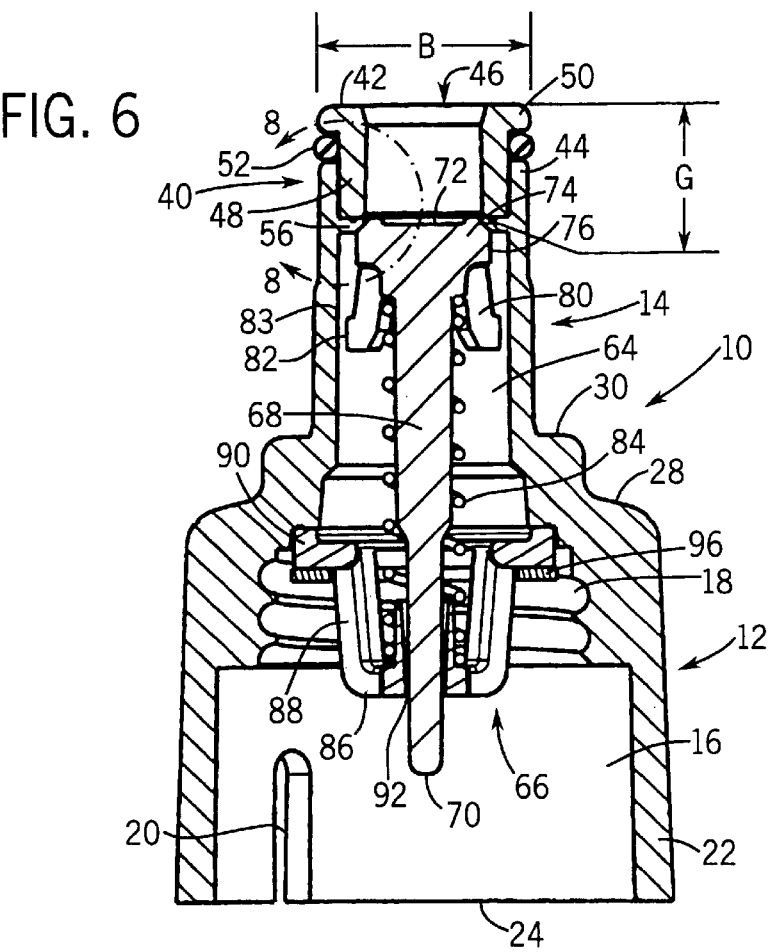
FIG. 6 is a section view taken along line 6—6 of FIG. 2.

Referring now to FIG. 2, the bottle adapter 10 includes a lower, screw cap portion 12 and an upper, probe portion 14. The screw cap portion 12 defines an open interior 16, as shown in FIG. 6. The open interior 16 is sized to receive the threaded mouth of an anesthetic bottle and guide the threaded mouth of the anesthetic bottle into engagement with agent-specific internal threads 18. The agent-specific threads 18 are configured to receive a specific type of anesthetic agent such that the bottle adapter 10 can be screwed onto the top of only one type of anesthetic bottle.

Figure 5:
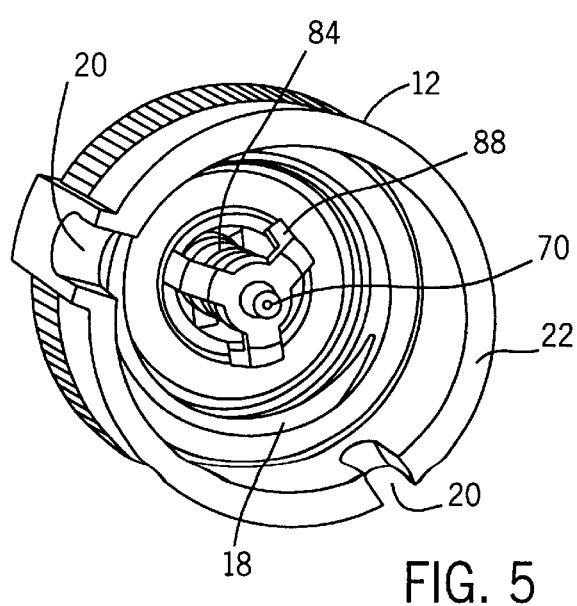
FIG. 5 is a back, perspective view showing the interior of the bottle adapter.

As can be seen in FIGS. 5 and 6, the screw cap portion 12 includes a pair of agent-specific receiving slots 20. The receiving slots 20 extend longitudinally into outer wall 22 from a first end 24 of the screw cap portion 12. The receiving slots 20 are sized to receive protrusions formed on the collar of the anesthetic bottle. The protrusions formed on the collar of the anesthetic bottle are spaced from each other by an angle dictated by the type of anesthetic agent contained within the bottle. Thus, the angle between the protrusions on the anesthetic bottle indicates the type of anesthetic agent contained within the specific bottle.

As illustrated in FIG. 5, the receiving slots 20 are spaced around the cylindrical outer circumference of the screw cap portion 12 by a specific angle. The angle between the receiving slots 20 corresponds to the agent-specific angle between protrusions on the anesthetic bottle. The corresponding angle between the protrusions on the anesthetic bottle and the slots 20 insures that the bottle adapter 10 can be installed on only the correct type of anesthetic agent.

In addition to including the receiving slots 20, the bottle adapter 10 is colored depending upon the type of anesthetic bottle upon which it will be used. Under the ISO standard, the anesthetic agent Isoflurane is colored purple, the anesthetic agent Halothane is colored red, the anesthetic agent Enflurane is colored orange and the anesthetic agent Sevoflurane is colored yellow. The bottle adapter 10 is preferably formed from nylon and colored in accordance with the ISO standard.

Referring back to FIG. 2, the screw cap portion 12 includes a series of closely spaced ribs 26 that provide a gripping surface for the screwing motion required to attach the bottle adapter 10 to the threaded mouth of an anesthetic bottle.

As shown in FIG. 6, the screw cap portion 12 is integrally formed with the probe portion 14. The probe portion 14 has an outer diameter significantly less than the screw cap portion 12. The outer diameter of the bottle adapter 10 decreases from the screw cap portion 12 to the probe portion 14 and forms a first shoulder 28 and a second shoulder 30.

Figure 3:
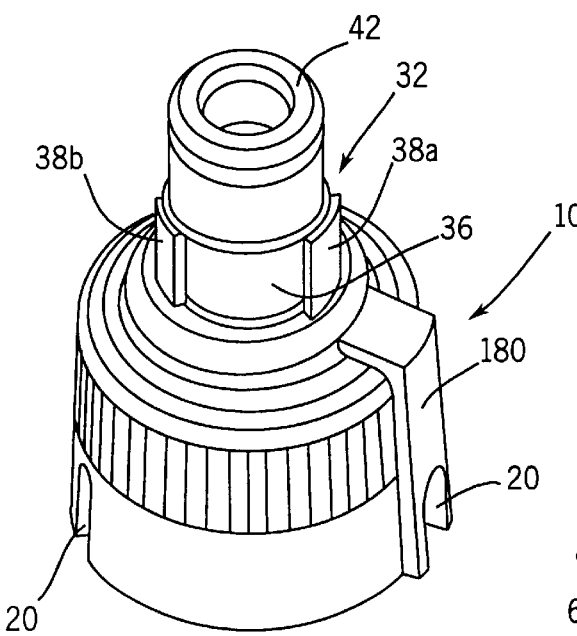
FIG. 3 is a perspective view of the bottle adapter.

As can best be seen in FIG. 2, the probe portion 14 includes a keyed section 32 that extends from the shoulder 30 to an upper end 34. The keyed section 32 includes a smooth outer surface 36 that defines an outer diameter of the keyed section 32. As illustrated in FIGS. 2 and 3, the keyed section 32 includes a pair of indexing ridges 38a and 38b that extend outward from the smooth outer surface 36. The indexing ridges 38a and 38b are used to insure the correct type of anesthetic agent is used with the anesthetic vaporizer, in a manner to be described in greater detail below.

Figure 7:
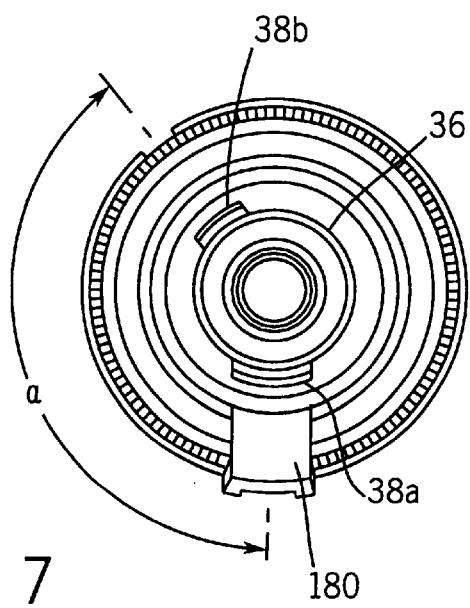
FIG. 7 is a top view of the bottle adapter illustrating a pair of indexing ridges.

As can be seen in FIG. 7, the indexing ridge 38a protrudes from the outer surface 36 and is separated from the indexing ridge 38b by the angle α. In the embodiment of the invention illustrated in FIG. 7, the angle α is 140°, which is the angle assigned to the anesthetic agent Isoflurane. The angle α between the indexing ridges 38a and 38b varies depending upon the type of anesthetic agent contained within the anesthetic bottle to which the bottle adapter 10 is attached. For example, the angle α is 160° for the anesthetic agent Halothane, the angle α is 200° for the anesthetic agent Enflurane and the angle α is 230° for the anesthetic agent Sevoflurane. These four examples are meant for illustrative purposes only, since the angle α between the indexing ridges 38a and 38b is set for each of the specific anesthetic agents currently available. This angle also corresponds to the angle between the protrusions on the collar of an anesthetic bottle as set by ISO 5360:1993. As can be seen in FIG. 3, the indexing ridges 38a and 38b are generally aligned with the receiving slots 20.

Figure 9:
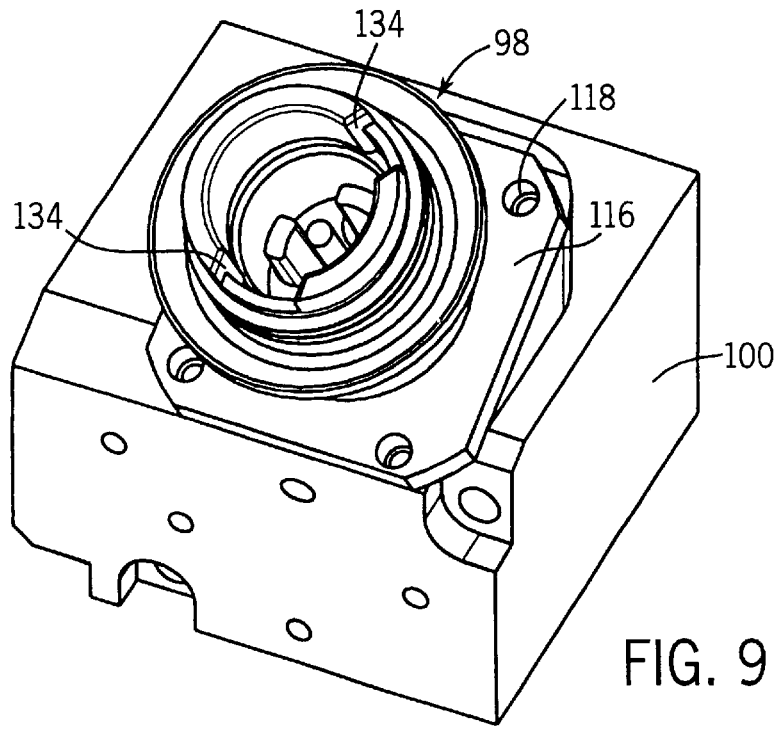
FIG. 9 is a perspective view of a filling station included on an anesthetic vaporizer that receives the bottle adapter.

As can be seen in FIG. 7, the indexing ridge 38a has a width greater than the width of the indexing ridge 38b. As can be seen in FIG. 9, the corresponding indexing groove in the vaporizer filler is a frontally located indexing groove that is positioned in the same place for each type of anesthetic agent. The wide indexing ridge 38a is aligned with a prominent ridge on the screw cap portion for all anesthetic agents, which may be easily and conveniently located for alignment with the groove in the front of the filler. The position of the indexing ridge 38b around the keyed section 32 with respect to the indexing ridge 38a varies depending upon the type of anesthetic agent being used.

Referring back to FIGS. 2 and 3, the probe portion 14 includes an adapter probe section 40 that extends from the upper edge 34 of the keyed section 32 to a top edge 42. The adapter probe section 40 has an outer diameter that is slightly less than the outer diameter of the outer surface 36 of the keyed section 32.

Referring now to FIG. 6, the outer wall 44 of the adapter probe section 40 defines an open interior that receives an end piece 46. The end piece 46 is defined by a cylindrical outer wall including a top lip 50. The cylindrical outer wall is sized to be received within the open area defined by the outer wall 44.

Figure 8:
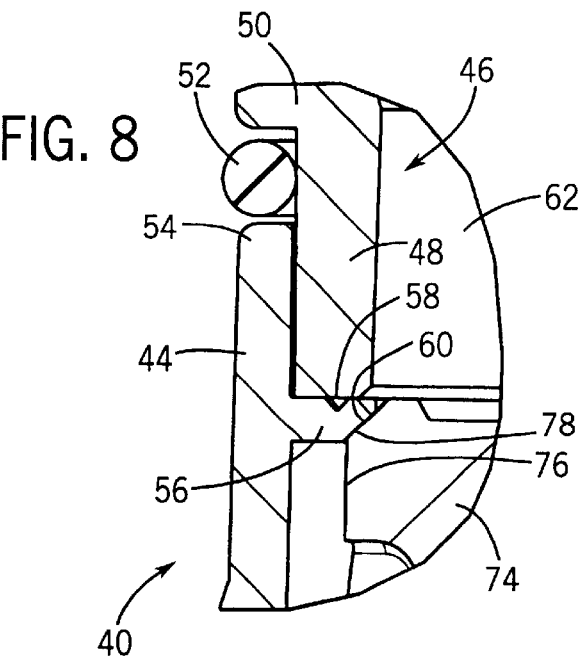
FIG. 8 is a magnified section view illustrating the area shown by line 8—8 in FIG. 6.

Referring now to FIG. 8, the end piece 46 includes a sealing ring 52 around its outer circumference. The sealing ring 52 is entrapped between the top lip 50 and the top edge 54 of the outer wall 44. The sealing ring 52 provides for a gas-tight seal between the probe portion 14 and the anesthetic vaporizer filling station, as will be described in much greater detail below.

As illustrated in FIG. 8, the outer wall 44 includes an inwardly extending annular flange 56. The annular flange 56 supports the bottom edge 58 of the end piece 46. In the preferred embodiment of the invention, both the bottle adapter 12 and the end piece 46 are formed from nylon. The end piece 46 is sized such that the end piece 46 can be ultrasonically welded or otherwise bonded to the outer wall 44 of the adapter probe section 40 to form a continuous member.

The annular flange 56 includes a conical seat 60 formed at its inner edge. The conical seat 60 generally defines an opening that is in communication with the open passageway 62 defined by the end piece 46. As illustrated in FIG. 6, the opening defined by the flange 56 is aligned with the open interior 64 such that anesthetic agent can flow from the anesthetic bottle through the probe portion 14 and out of the bottle adapter 10 through the end piece 46.

Figure 4:
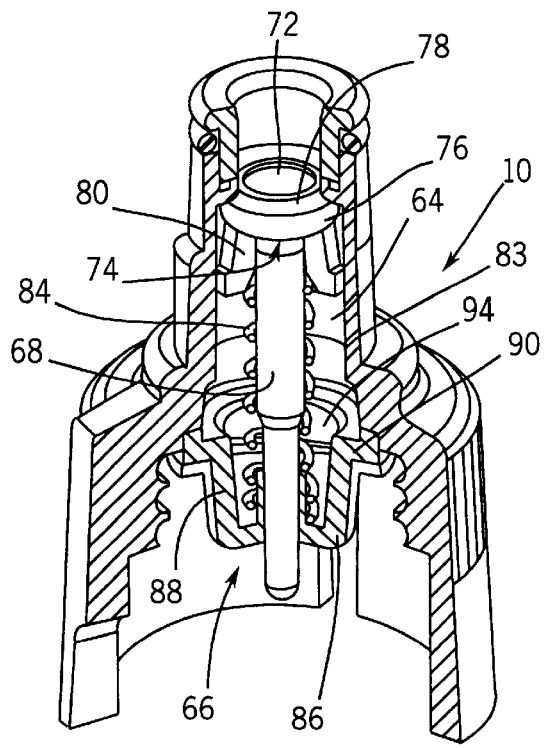
FIG. 4 is a partial cutaway perspective view of the bottle adapter shown in FIG. 3.

Referring now to FIGS. 4 and 6, the bottle adapter 10 includes an adapter valve assembly 66 that is movable between an open position and a closed position to control the flow of anesthetic agent from the anesthetic bottle to which the bottle adapter 10 is attached. The adapter valve assembly 66 includes an elongated valve stem 68 that extends from a first end 70 to a second end 72. The second end 72 of the valve stem 68 includes a valve head 74. The valve head 74 is defined by a cylindrical outer surface 76 that is joined to a conical sealing surface 78, as illustrated in FIG. 4. As can be seen in FIG. 8, the outer surface 76 has a diameter greater than the diameter of the opening formed by the flange 56, which prevents the valve head 74 from passing through the opening defined by the flange 56. The conical sealing surface 78 formed on the valve head 74 contacts the conical seat 60 to provide a seal when the valve stem 68 is biased into contact with the flange 56.

Referring back to FIGS. 4 and 6, the valve head 74 further includes a plurality of guide fingers 80 that depend from the outer surface 76. The guide fingers 80 each include a lateral guide surface 82 that contacts the inner surface 83 defining the open interior 62 to guide the valve head 74 during its opening and closing movement. The guide fingers 80 are designed to maintain continuity of the single flow passage around the open interior 62 of the bottle adapter and act with an angle of operation of 15 to 35 degrees from vertical to allow gravity to assist in separating liquid and gas during the filling process.

Referring back to FIGS. 4 and 6, the adapter valve assembly 66 is biased to a closed position by a bias spring 84. The bias spring 84 has a first end in contact with the valve head 74 and a second end supported within a mounting cage 86. The mounting cage 86 includes three support legs 88 that extend upward and are joined to an annular flange 90. The annular flange 90 is supported at the top of the agent-specific threads 18. As can be seen in FIG. 6, the first end 70 of the valve stem 68 extends through a central opening 92 such that the entire valve stem 68 can move relative to the stationary mounting cage 86. As illustrated in FIG. 4, the annular flange 90 of the mounting cage 86 defines a central opening 94 that is aligned with the open interior 64 such that the anesthetic agent can flow from the anesthetic bottle through the bottle adapter 10 and out of the end piece 46.

Referring back to FIG. 6, a resilient washer 96 is positioned in contact with the annular flange 90 to provide a seal between the annular flange 90 and an anesthetic bottle. In this manner, the anesthetic agent within the anesthetic bottle is prevented from flowing out of the first end 24 of the bottle adapter 10.

In FIGS. 2–8, the bottle adapter 10 that forms half of the anesthetic vaporizer filling system of the present invention has been described. Referring now to FIGS. 9–12, the second half of the anesthetic vaporizer filling system of the present invention will now be described. The second half of the filling system is a unique filling station 98 associated with the anesthetic vaporizer 9. The filling station 98 is configured to receive the bottle adapter 10 and allow the anesthetic agent to be discharged from the anesthetic bottle 8 attached to the bottle adapter and fill and internal sump within the vaporizer, as shown in FIG. 1.

Figure 10:
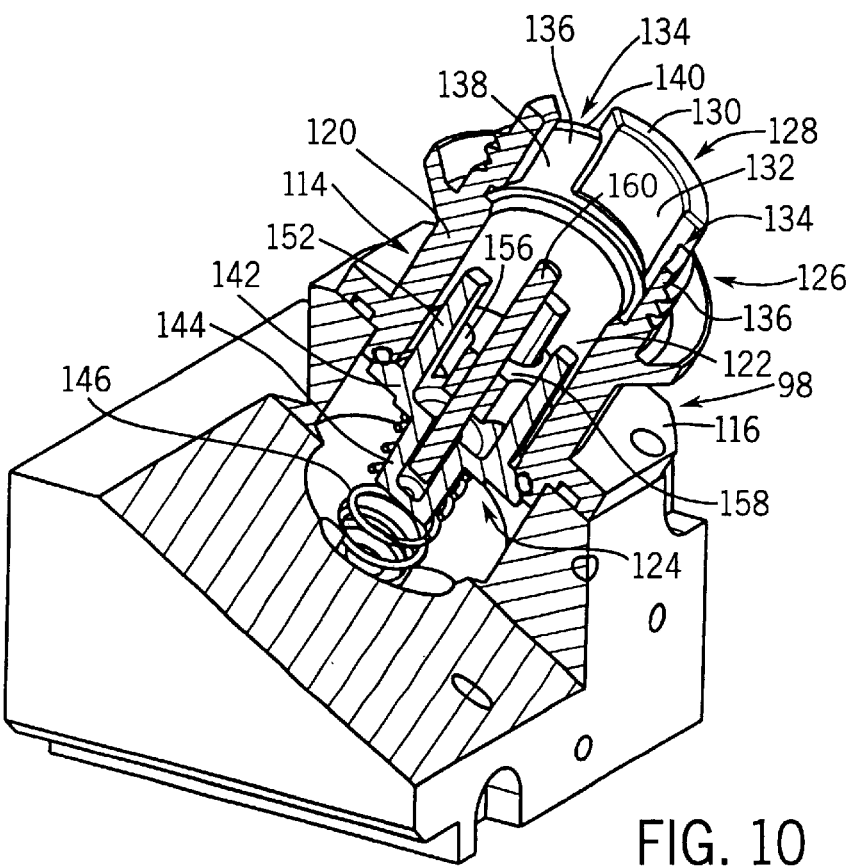
FIG. 10 is a perspective, partial section view of the filling station of FIG. 9.
Figure 12:
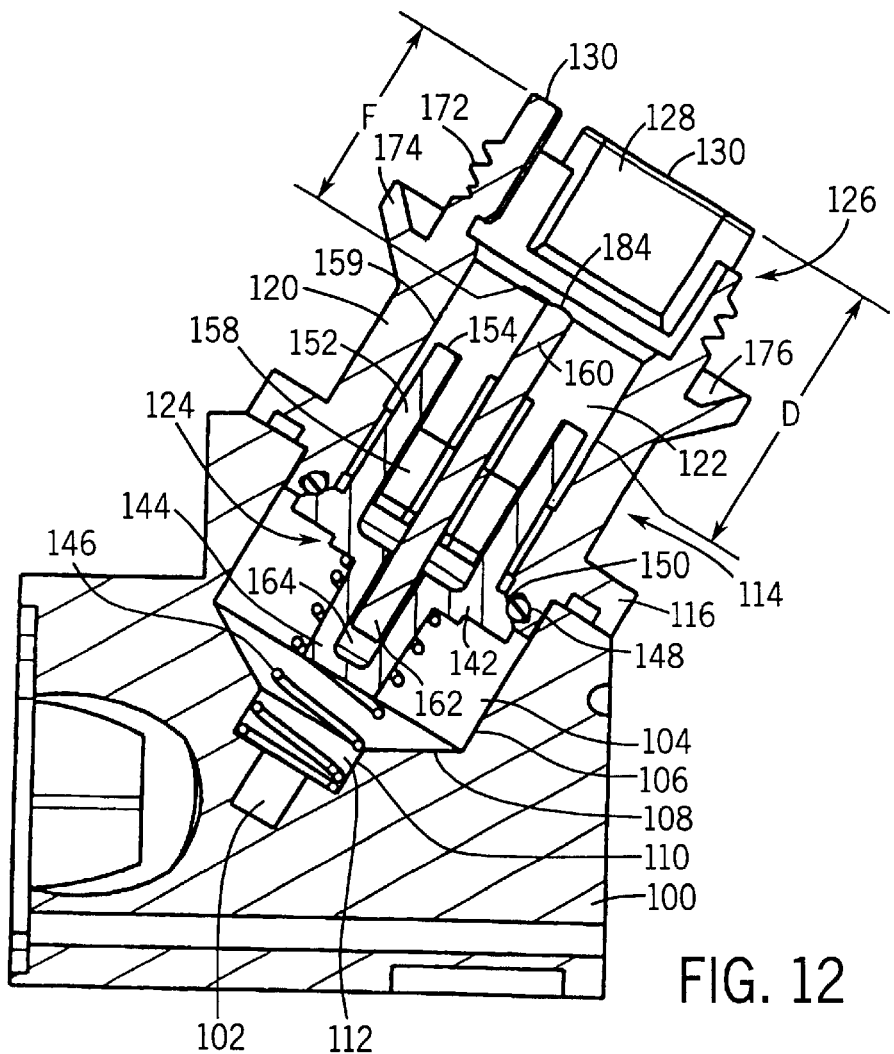
FIG. 12 is a section view of the filling station of the anesthetic vaporizer filling system of the present invention.

As can be seen in FIGS. 9 and 10, the filling station 98 is positioned on a mounting block 100 positioned within the anesthetic vaporizer. As illustrated in FIG. 12, the mounting block 100 includes an internally bored passageway 102 that leads to the internal sump of the vaporizer. The mounting block 100 further includes an internal cavity 104 that is bored from the otherwise solid mounting block 100. The internal cavity 104 is defined by a generally cylindrical outer wall 106 and is positioned at an angle relative to vertical. The outer wall 106 is joined to a conical wall 108 that in turn is joined to a cylindrical lower wall 110. The lower wall 110 defines a spring cavity 112 that is in fluid communication with the passageway 102.

Referring now to FIGS. 10 and 12, the filling station 98 is defined by a filler body 114. The filler body 114 includes an attachment flange 116 having a plurality of attachment holes 118 that allow the filler body to be securely attached to the mounting block 100, as best illustrated in FIG. 9. Referring back to FIGS. 10 and 12, the filler body 114 is a metallic member generally defined by a cylindrical outer wall 120 that defines open interior 122. The open interior 122 receives a portion of a filler valve 124, as will be described in much greater detail below.

The filler body 114 defines a filler spout 126 configured to direct and receive the keyed section 32 of the bottle adapter. Specifically, the filler spout 126 is defined by a cylindrical outer wall 128 including a top edge 130. The inner circumference of the outer wall 128 corresponds to the outer diameter of the smooth outer surface 36 of the keyed section 32, as illustrated in FIG. 2. Thus, when the bottle adapter 10 is inserted into the filling station 98, the outer surface 36 contacts the inner surface 132 of the outer wall 128.

In order to accommodate the protruding indexing ridges 38a and 38b formed on the bottle adapter 10, the filler spout 126 of the filling station 98 includes a pair of indexing grooves 134 as shown in FIGS. 9 and 10. The indexing grooves 134 are spaced by the same angle α that defines the spacing between the indexing ridges 38 on the bottle adapter, as illustrated in FIG. 7.

Referring back to FIGS. 9 and 10, each of the indexing grooves 134 are defined by a wall portion 136. The wall portion 136 has a thickness less than the thickness of the outer wall 128 such that the indexing groove 134 is formed by the difference in diameter between the inner surface 132 of the outer wall 128 and the inner surface 138 of the wall portion 136. In addition to having a thickness less than the outer wall 128, each of the wall portions 136 defines a top end 140 spaced slightly below the top edge 130 of the outer wall 128. The spacing between the top edge 140 and the top edge 138 provide the user with a visual indication of the location for each of the indexing grooves 134.

Figure 14:
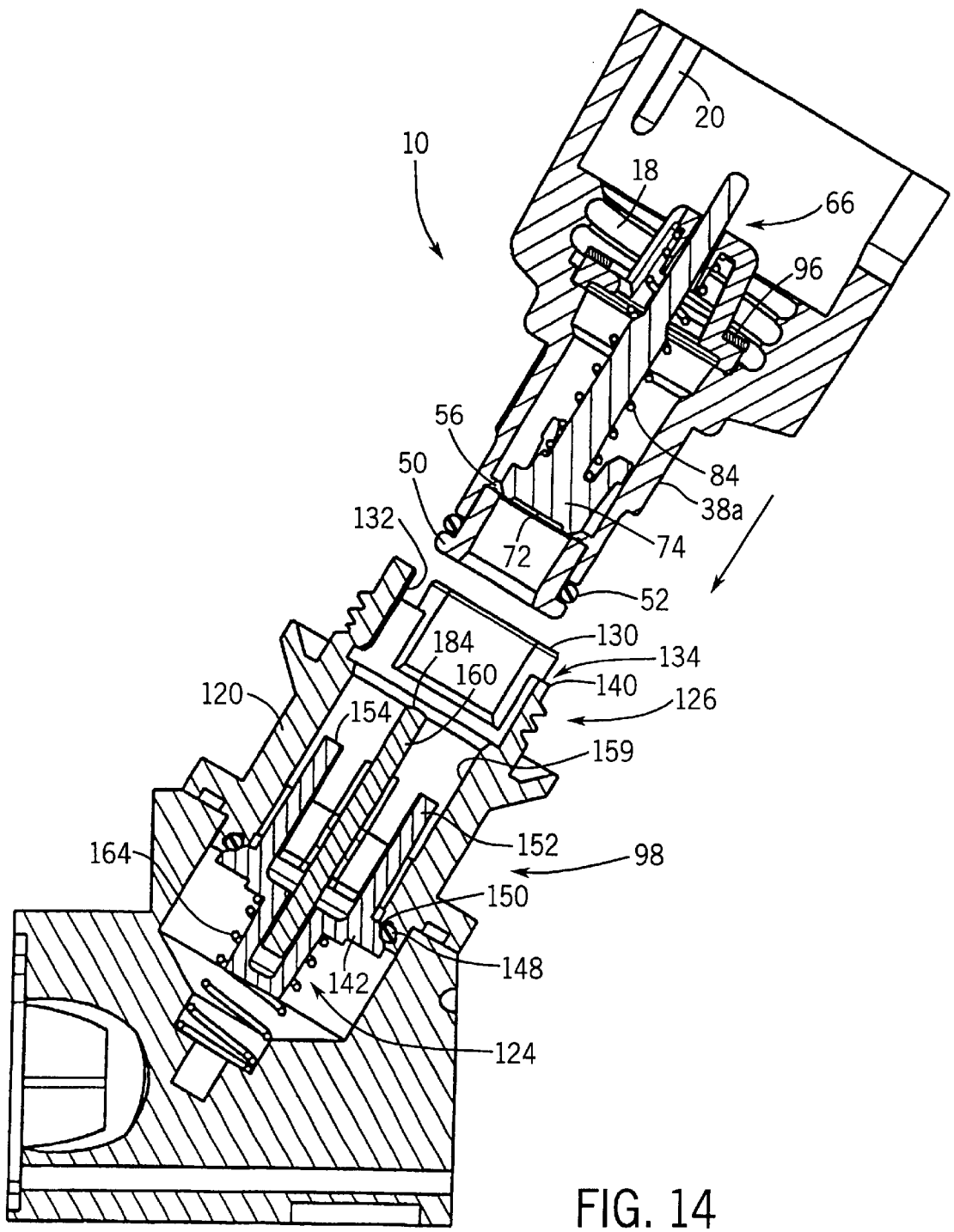
FIG. 14 is a section view illustrating the bottle adapter and filling station in their separated position.

Referring now to FIG. 12 and FIG. 14, the inner diameter of the open interior 122 is slightly less than the inner diameter of the filler spout 126 such that the probe section 40 of the bottle adapter 10 can be initially inserted into the filling station 98 without resistive force due to compression of the seal 52 against the walls of the filler spout 126.

Referring now to FIGS. 10 and 12, the filler valve assembly 124 includes a valve body 142. The valve body 142 includes a lower section 144 that is surrounded by a bias spring 146. The bias spring 146 is supported at its first end with the spring cavity 112 and is in contact with the valve body 142 at its second end. In this manner, the bias spring 146 urges the valve body 142 into the closed, bias position illustrated in FIG. 12. A resilient seal 148 is positioned between the filler body 114 and a conical sealing surface 150 formed on the valve body 142. The seal 148 prevents the flow of an anesthetic agent into the internal cavity 134 until the filler valve 124 has been opened.

Figure 11:
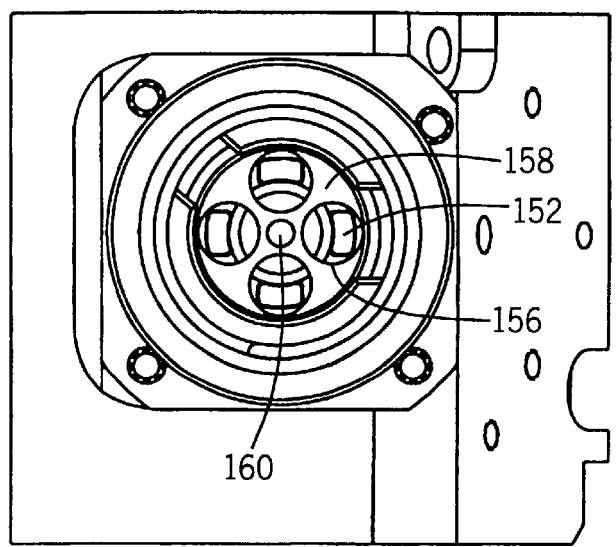
FIG. 11 is a top view of the filling station illustrated in FIG. 9.

The filler valve body 142 further includes a plurality of projecting legs 152. The projecting legs 152 extend into the open interior 122 and are each defined by a top edge 154. As can be seen in FIGS. 10 and 11, each of the projecting legs 152 extends through a cylindrical opening 156 formed in a stationary mounting block 158. The mounting block 158 is secured to the inner surface 159 of the outer wall 120 and is stationary within the open interior 122.

As illustrated in FIGS. 10 and 12, the mounting block 158 includes a stationary activation rod 160. The stationary activation rod 160 is secured to the mounting block 158 and extends along the center axis of the filler body 114, as illustrated in FIG. 11. Since the stationary activation rod 160 is secured to the mounting block 158, the activation rod 160 does not move during operation of the filler valve 124.

Referring now to FIG. 12, the lower end 162 of the activation rod 160 is received within a guide cavity 164 formed in the lower section 144 of the valve body 142. The interaction between the guide cavity 164 and the stationary rod 160 guides the movement of the valve body 142 during opening and closing of the filler valve assembly 124.

Figure 13:
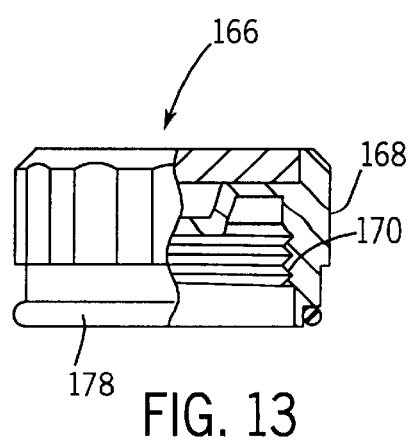
FIG. 13 is a partial section view illustrating a filler cap used to close the filling station of FIG. 12 when the filling station is not receiving a bottle of anesthetic agent.

Referring now to FIG. 13, thereshown is a filler cap 166 that can be installed onto the filling station 98 when the filling station 98 is not receiving a bottle of anesthetic agent. The filler cap 166 includes an outer surface that can be grasped by a user to attach the filler cap 166. The filler cap 166 includes a series of internal threads 170 that engage corresponding external threads 172 formed on the filler spout 126, as illustrated in FIG. 12. The outer threads 172 extend along the filler spout 126 until they reach a rim 174. The rim 174 includes a conical sealing surface 176. The conical sealing surface 176 receives a resilient sealing ring 178 formed near the bottom edge of the filler cap 166, as shown in FIG. 13. The interaction between the sealing ring 178 and the conical sealing surface 176 provides a seal for the filling station 98 when an anesthetic agent is not-being used. The filler cap 166 therefore prevents contamination from the environment and prevents contaminating debris from entering into the filler spout 126. In the preferred embodiment of the invention, the filler cap 166 is permanently attached to the vaporizer by a flexible cord that prevents the filler cap 166 from being lost.

Referring now to FIGS. 14–17, the method and steps required to fill the anesthetic vaporizer using the anesthetic vaporizer filling system of the present invention will now be described. When it is desired to fill the vaporizer with more liquid anesthetic agent, the bottle adapter 10 is attached to the threaded top end of the anesthetic bottle. Specifically, the threaded end of the anesthetic bottle is received within the agent-specific threads 18 formed in the bottle adapter 10. As the bottle is screwed into registration with the threads 18, the top end of the bottle contacts the resilient washer 96 to provide a liquid tight seal between the bottle adapter 10 and the anesthetic bottle. As described, the receiving slots 20 formed in the bottle adapter 10 correspond to protrusions contained on the anesthetic bottle to insure that the correct type of bottle adapter can only be installed upon the correct type of anesthetic bottle.

Once the bottle adapter 10 has been securely attached to the anesthetic bottle, the bottle adapter 10 can be inserted into the filling station 98, as illustrated in FIG. 14. As can be seen in FIG. 4, the bottle adapter 10 includes a protruding visual guide 180 that is aligned with the primary receiving slot 20. The visual guide 180 allows the user to easily identify a known location on the bottle adapter 10. Once the user has identified the visual guide 180, the bottle adapter 10 is rotated until the visual guide 180 is aligned with the lower indexing groove 134 formed in the filler spout 126, as shown in FIG. 14. As described, each of the indexing grooves 134 is defined by a top edge 140 recessed from the top edge 130 of the filler spout 126 to aid in the alignment of the bottle adapter 10 with the filling station 98.

Once the bottle adapter 10 has been aligned, the bottle adapter 10 is moved into engagement with the filling station 98. In the preferred embodiment of the invention, the width B of the end piece 46 (FIG. 6) is less than the diameter of the filler spout 126, as defined by the inner surface 132. Thus, when the bottle adapter 10 is initially brought into engagement with the filling station 98, the seal 52 does not cause resistive force against the inner surface 132 of the filler spout 126.

As the bottle adapter 10 continues its movement into the filling station 98, the indexing ridges 38$a$ and 38$b$ of the bottle adapter are received within the corresponding indexing grooves 134 formed on the filler spout 126. If the proper bottle adapter 10 is being utilized for the filling station 98, the interaction between the indexing ridges 38$a$ and 38$b$ and the indexing grooves 134 allow the bottle adapter 10 to be moved further into engagement with the filling station 98. However, if the bottle adapter 10 is incorrect for the filling station 98, the interference between the indexing ridges 38$a$ and 38$b$ of the bottle adapter 10 and the indexing grooves 134 of the filling station 98 will prevent further movement.

After the indexing ridges 38$a$ and 38$b$ of the bottle adapter are received within the corresponding indexing grooves 134 formed on the filler spout 126, the sealing ring 52 contacts the inner surface 159 of the outer wall 120. The interaction between the sealing ring 52 and the inner surface 159 provides a gas-tight seal. The gas-tight seal created by the sealing ring 52 prevents the gas pressure within the vaporizer from being vented to atmosphere when the filler valve assembly 124 is opened. It is important to note that the dimensions of the filling system components are selected such that neither the adapter valve assembly 66 nor the filler valve assembly 124 opens prior to the keyed interaction between the bottle adapter 10 and the filling station 98 and creation of the gas-tight seal caused by the contact of sealing ring 52 and inner surface 159. Therefore, anesthetic agent is not released from the anesthetic bottle prior to proper identification of the type of anesthetic agent being dispensed, and the creation of a gas tight seal enclosing the fluid path during the filling process.

Figure 15:
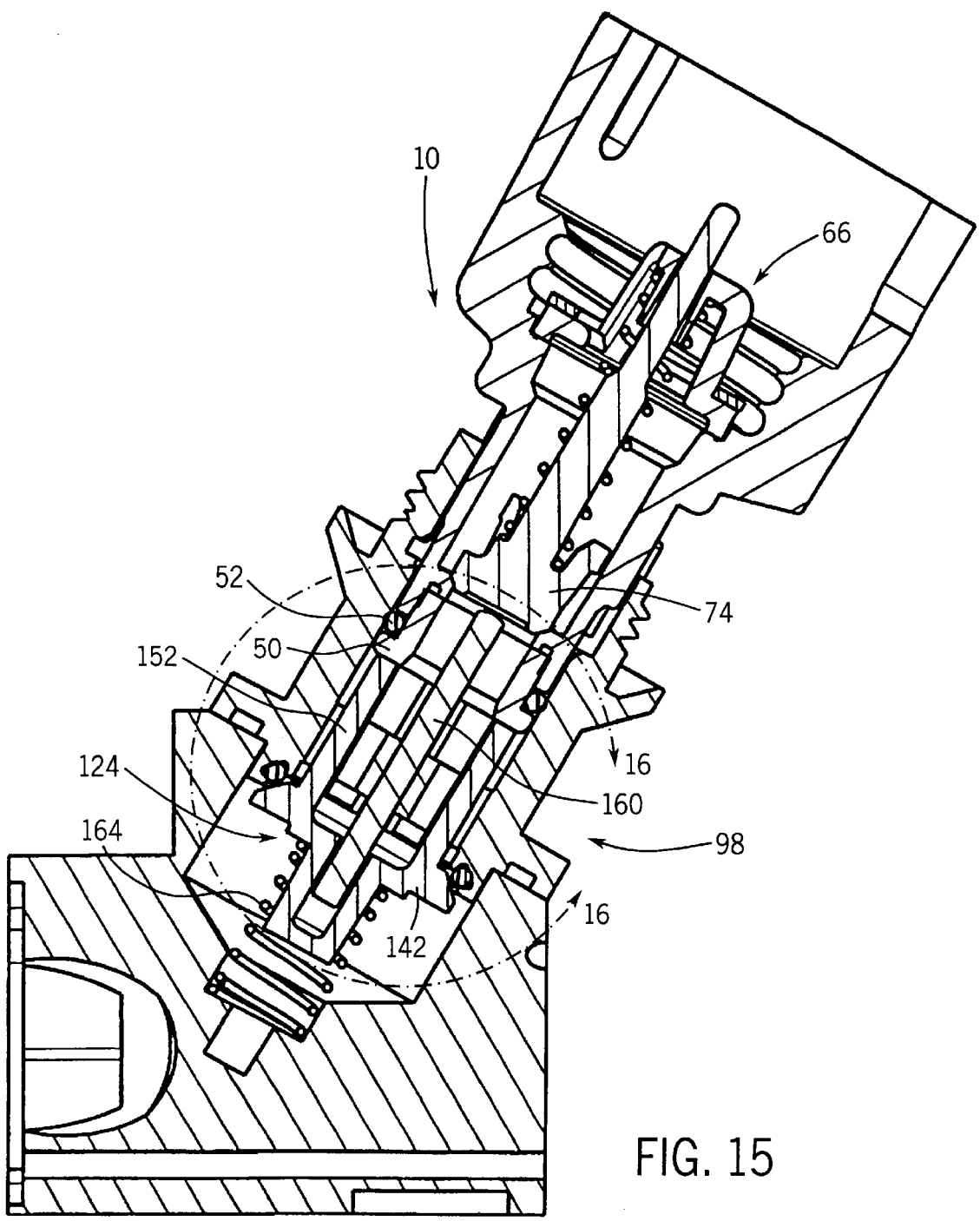
FIG. 15 is a section view illustrating the bottle adapter being inserted into the filling station and the opening of the filler valve assembly prior to opening of the adapter valve assembly.
Figure 16:
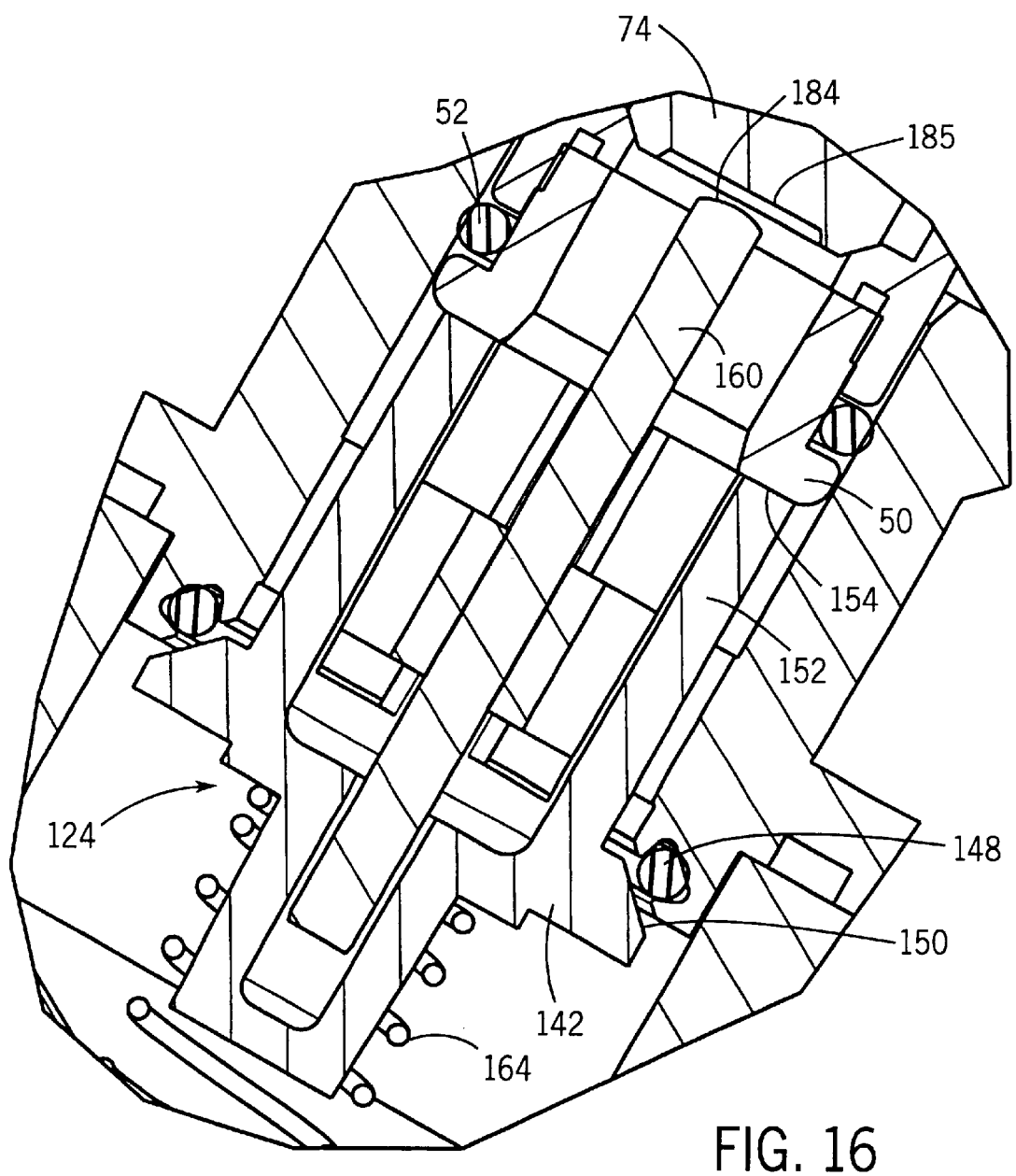
FIG. 16 is a magnified view of the area illustrated by line 16—16 in FIG. 15.

Once the indexing ridges 38$a$ and 38$b$ are received within the corresponding indexing grooves 134, the bottle adapter 10 is moved further into the filling station 98, as shown in FIGS. 15 and 16. During this movement, the top lip 50 of the bottle adapter 10 contacts the top edge 154 of each projecting leg 152. The further movement of the bottle adapter 10 pushes the entire valve body 142 downward against the bias spring 164. As the valve body 142 moves, the conical sealing surface 150 moves away from the seal 148.

As shown in FIG. 12, the distance F from the top end 184 of the activation rod 184 to the top edge 130 of the filler spout 126 and the distance D from the top edge 154 of each projecting leg 152 to the top edge 130 are selected such that the filler valve assembly 124 is opened prior to opening of the bottle adapter valve assembly 60. Referring back to FIG. 16, the top end 184 of the activation rod 160 remains spaced from the recessed face surface 185 of the valve head 74 as the filler valve assembly 124 is opened. The recessed face surface 185 is located a distance G from the top edge 42 of the lip 50, as illustrated in FIG. 6.

As the valve body 142 moves away from the seal 148, the sealing ring 52 prevents the release of pressure within the anesthetic vaporizer to atmosphere. The filling station 98 can therefore be used with high pressures in the vaporizer.

Figure 17:
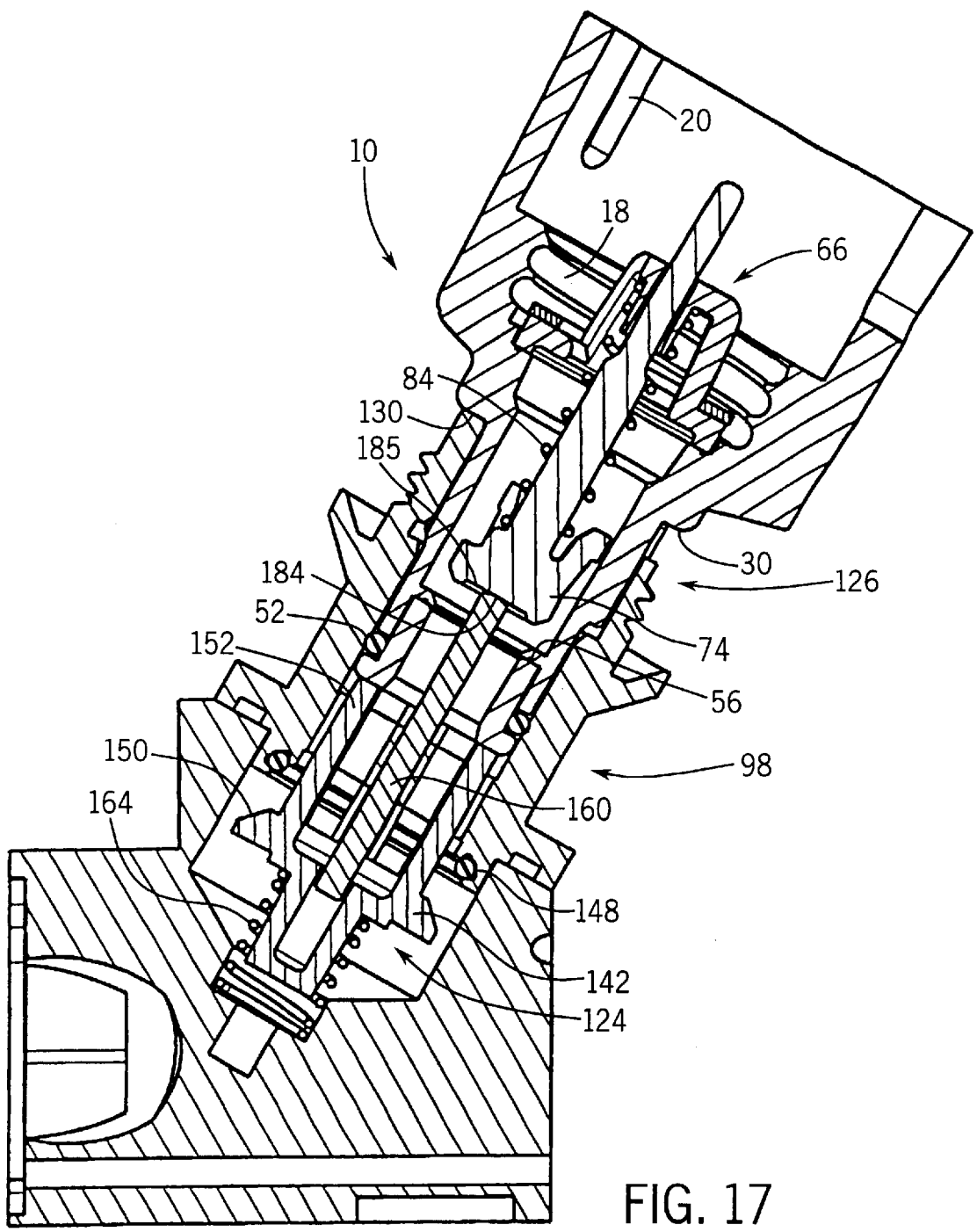
FIG. 17 is a section view illustrating the bottle adapter and filling station in a filling position.

As the bottle adapter 10 continues to move downward into the filling station 98, the top end 184 of the stationary activation rod 160 contacts the recessed face surface 185 of the valve head 74, as shown in FIG. 17. The stationary activation rod 160 pushes the valve head 74 away from the annular flange 56 against the force of the bias spring 84. Thus, the stationary activation rod 160 causes the adapter valve assembly 66 to open and allows the anesthetic agent to flow into the filling station 98 by the force of gravity.

Once the bottle adapter 10 has been completely positioned within the filling station 98, as illustrated in FIG. 17, the top edge 130 of the filler spout 126 contacts the second shoulder 30 to securely support the bottle adapter 10 and connected bottle as illustrated. In this position, both the bottle adapter valve assembly 66 and the filler valve assembly 124 are open, which allows the anesthetic agent to flow freely into the sump of the anesthetic vaporizer.

Once the anesthetic bottle has been emptied, the bottle adapter 10 is moved out of engagement with the filling station 98. During this movement, the valve head 74 moves back into contact with the annular flange 56 to seal the bottle adapter 10. Further movement of the bottle adapter 10 out of the filling station 98 causes the conical sealing surface 150 to engage the seal 148, thus closing the filler valve assembly 124. Finally, the sealing ring 52 leaves engagement from the inner surface 159 and the bottle adapter is completely removed. As can be understood by this sequence of operation, during removal the adapter valve assembly 66 is closed first to prevent the flow of any further anesthetic agent out of the bottle adapter. Since the filler valve assembly 124 is still open when the bottle adapter valve assembly 66 closes, any anesthetic agent that has left the bottle can pass through the filler valve assembly 124 and into the vaporizer sump. On occasions where the adapter is removed too rapidly for this liquid to drain to the vaporizer, or when the vaporizer is so filled that the internal passages of the bottle adapter 10 and filling station are entirely filled with liquid, liquid which cannot drain to the vaporizer remains in the generally upward facing open interior 122 of the filler valve body, and is captured by replacement of the filler cap 166.

In the embodiment of the invention illustrated, the bottle adapter 10 is described as being removable from each anesthetic bottle to be discharged. However, it is contemplated by the inventors that the bottle adapter 10 could be permanently attached to an anesthetic bottle while operating within the scope of the invention. Further, it is contemplated by the inventors that the bottle adapter could be permanently affixed to the anesthetic vaporizer or attached and stored in a removable manner to the anesthetic vaporizer for attachment to the anesthetic bottle in this location. Further, it is contemplated by the inventors that the filling station 98 could include a band, label, feature or cover of color typically associated with the type of anesthetic agent to be used. The color-coding configuration for the filling station would be the same as the ISO standard used on the bottle adapter 10.

Figure 18:
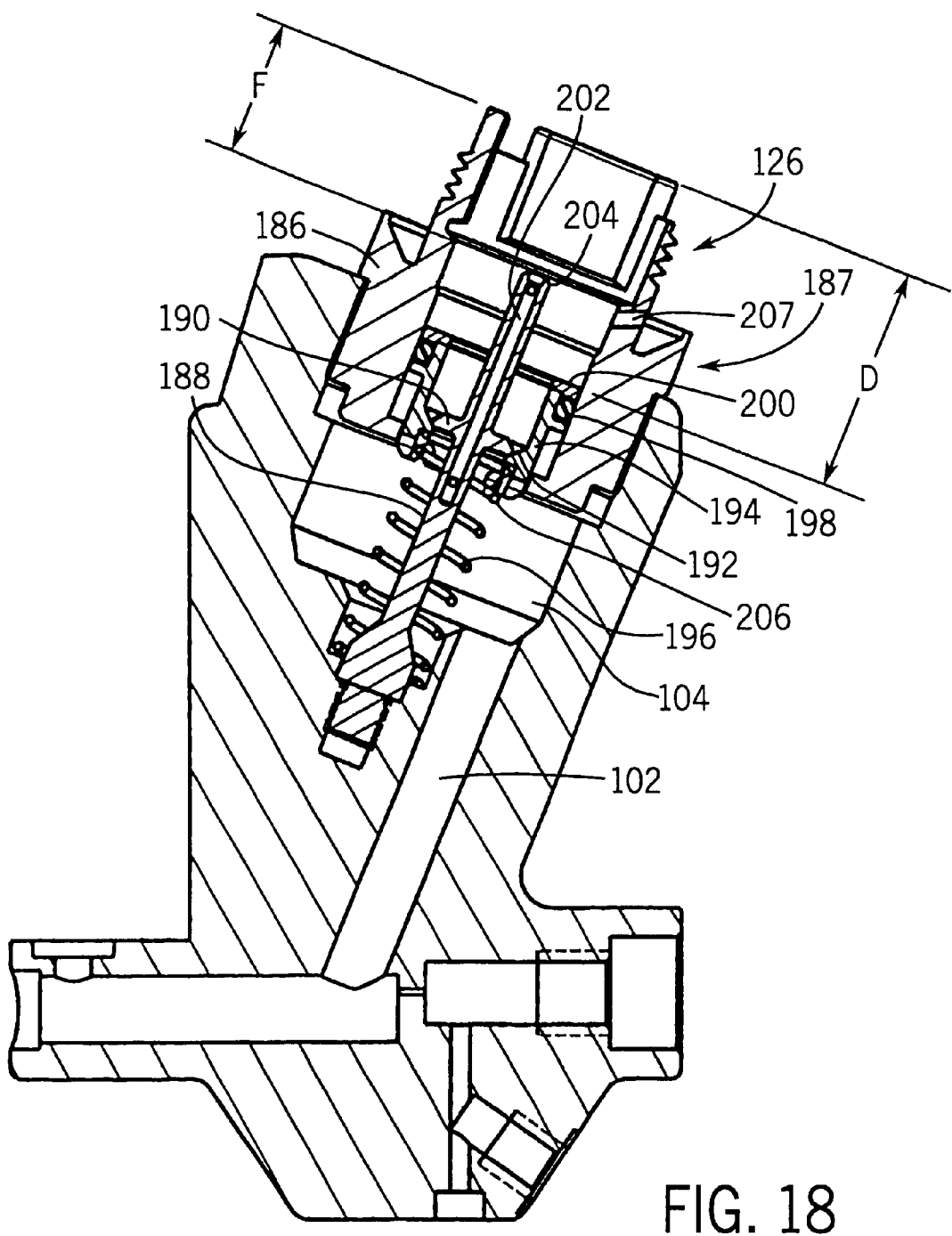
FIG. 18 is a section view of a second embodiment of a filling station constructed in accordance with the present invention.
Figure 19:
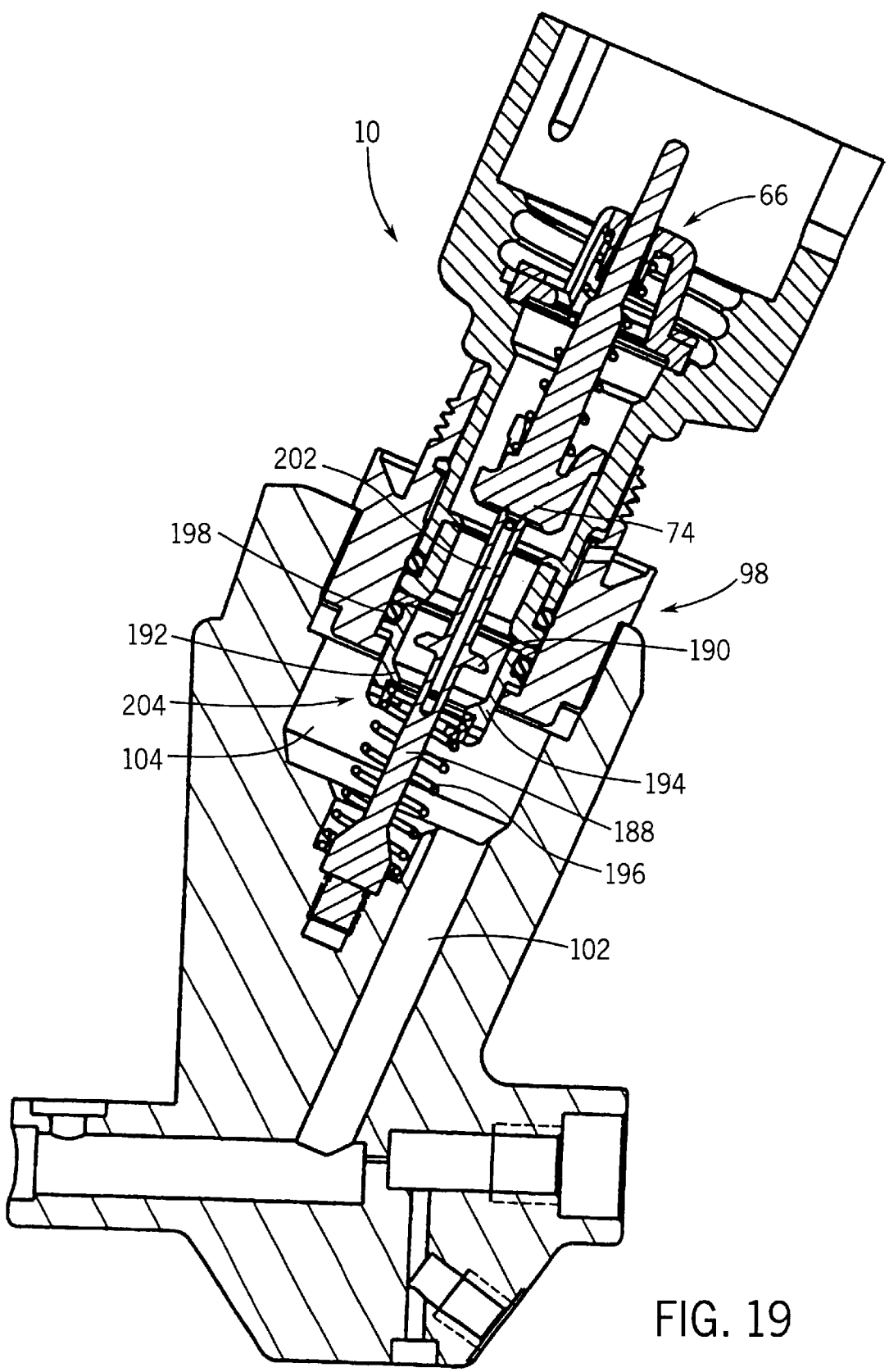
FIG. 19 is a section view illustrating the second embodiment of the filling station allowing anesthetic agent to be transferred from a bottle joined to the bottle adapter.

Referring now to FIG. 18, thereshown is a second embodiment of a filling station 187 of the present invention. The filling station 187 shown in FIG. 18 is useful with vaporizers that do not include high internal pressures and includes a filler body 186 and a stationary activation rod 188. The activation rod 188 includes a sealing flange 190. The sealing flange 190 engages a conical sealing surface formed on a valve body 194. The valve body 194 is movable relative to the activation rod 188 and is biased into a closed position by the bias spring 196. The valve body 194 includes a sealing ring 198 that engages the inner surface of the filler body 186 and provides a liquid seal on this surface over the entire operating travel of the valve body 194. The valve body is guided over the operating travel of the valve by the inner surface of the filler body 186. A flexible washer 200 contacts the top end of the bottle adapter when the bottle adapter is positioned within the filling station 98, as illustrated in FIG. 19. The filling station 187, as shown in FIG. 18, includes an identical filler spout 126, the features of which have been previously described.

As illustrated in FIG. 18, the center activation rod 188 includes an open passageway 202 that extends between an upper opening 204 and a lower opening 206. The upper opening 204 and the lower opening 206 are positioned on opposite sides of the sealing connection between the sealing flange 190 and the sealing surface 192.

The open passageway 202 allows alternative internal passageways to be employed within the vaporizer which require the passage of gas to equalize pressure across the filler valve, for example during draining of the vaporizer by means of some completely separate drain passage. The above opening 204 is positioned such that liquid incorrectly poured into the filler spout will preferentially drain out of the spout by means of passageway 207 rather than draining past the filler valve into the vaporizer. Additionally, the upper opening 204 is located in the side of the activation rod 188 rather than the end, so that any fluid ejected from this port for any reason due to misuse of the vaporizer, is not directed upwards, but harmlessly against the inner surface of the filler body 186.

The lower opening 206 connects to the internal cavity 104 which connects to the open passageway 102 to direct the anesthetic agent to the vaporizer sump.

As illustrated in FIG. 19, the fixed center activation rod 188 functions to move the valve head 74 to an open position to allow anesthetic agent from the bottle adapter 10 to enter into the filling station 98. Like the first embodiment previously described, the filler valve assembly 204 opens prior to the adapter valve assembly 66 as the bottle adapter 10 is brought into engagement with the filling station 98. Thus, comparing FIG. 19 and FIG. 14, the fixed center activation rod 188 is equivalent to activation rod 160 of the first embodiment and the valve body 194 including sealing ring 198 is together equivalent to valve body 142 of the first embodiment. The inner surface of the filler body 186, as regards guidance of the valve body 194, is equivalent to the lower part 162 of activation rod 160 which guides the movement of the valve body 142 in the first embodiment. The latter valve body 142 does not require a sealing ring such as 198 since the equivalent to sealing over the travel of the valve body 194 is provided by the fact that the valve body 142 surrounds the guidance member in such a way that no additional sealing over the guidance member is required.

Various alternatives and embodiments are contemplated as being within the scope of the following claims particularly pointing out and distinctly claiming the subject matter regarded as the invention.

We claim:

1. A filling system for the delivery of a liquid anesthetic agent from an anesthetic bottle to an internal sump of an anesthetic vaporizer, the system comprising:

a bottle adapter configured for attachment to the anesthetic bottle, the bottle adapter having an outlet opening through which anesthetic agent from the anesthetic bottle can be discharged;

an adapter valve assembly positioned in the bottle adapter and movable between an open position and a closed position, the adapter valve assembly including a valve head that prevents the flow of the anesthetic agent through the outlet opening when the adapter valve assembly is in the closed position;

a filling station positioned on the anesthetic vaporizer for receiving the bottle adapter and through which the anesthetic agent can flow into the internal sump of the anesthetic vaporizer; and a filler valve assembly positioned in the filling station and movable between an open position and a closed position, the filler valve assembly including a stationary activation rod configured to contact the valve head of the adapter valve assembly and move the adapter valve assembly to the open position as the bottle adapter is inserted into the filling station and a valve body movable within the filling station, the valve body being biased into a closed position to prevent the flow of anesthetic agent into the vaporizer, wherein the bottle adapter contacts the valve body and moves the valve body to the open position as the bottle adapter is inserted into the filling station.

2. The filling system of claim 1 wherein the adapter valve assembly and the stationary activation rod are positioned such that the adapter valve remains in the closed position until the bottle adapter probe is positioned inside the filling station.

3. The filling system of claim 2 wherein the adpater valve assembly and the filler valve assembly are positioned such that the filling valve assembly opens prior to the opening of the adapter valve assembly as the bottle adapter is inserted into the filling station.

4. The filling system of claim 1 wherein the filling station includes a cylindrical open interior defined by an inner wall and the bottle adapter includes a sealing ring formed along its outer surface, wherein the sealing ring contacts the inner wall of the filling station to form a gas-tight seal with the inner wall as the bottle adapter is inserted into the filling station.

5. The filling system of claim 4 wherein the sealing ring contacts the inner wall of the filling station prior to the bottle adapter opening the filler valve assembly to prevent the release of vapor pressure from the anesthetic vaporizer when the filler valve assembly opens.

6. The filling system of claim 1 wherein the filling station includes a cylindrical open interior sized to receive the bottle adapter, the activation rod being centered within the cylindrical open interior.

7. The filling system of claim 6 wherein the activation rod is securely mounted to a mounting block extending across and mounted to the open interior of the filling station, the mounting block having a plurality of flow openings extending therethrough, the flow openings allowing the anesthetic agent to flow through the mounting block.

8. The filling system of claim 7 wherein the valve body of the filler valve assembly includes a plurality of projecting legs that contact a top lip of the bottle adapter as the bottle adapter is inserted into the filling station, the projecting legs extending through the flow openings of the mounting block.

9. The filling system of claim 8 wherein the distance from a top end of the activating rod to a top edge of the projecting legs is less than the distance from the top lip of the bottle adapter to a face surface of the valve head, wherein the top lip of the bottle adapter contacts the projecting legs prior to contact between the activation rod and the valve head as the bottle adapter is inserted into the filling station.

10. The filling system of claim 1 further comprising:
a cylindrical keyed section formed on the bottle adapter having at least a pair of protruding indexing ridges positioned at a first angle relative to each other around the outer circumference of the keyed section; and
a filler spout formed on the filling station, the filler spout having a cylindrical outer wall including at least a pair of recessed indexing grooves positioned at a second angle relative to each other, wherein the indexing grooves receive the indexing ridges and allow the bottle adapter to be inserted into the filling station only when the first angle is equal to the second angle.

11. The filling system of claim 10 wherein the first angle between the indexing ridges and the second angle between the indexing grooves are determined by the type of anesthetic agent such that the filler spout can receive only one type of anesthetic agent.

12. The filling system of claim 11 wherein the indexing grooves of the filler spout contact and receive the indexing ridges of the keyed section prior to the filler valve assembly opening as the bottle adapter is inserted into the filling station.

13. The filling system of claim 10 wherein the filling station includes a cylindrical open interior defined by an inner wall and the bottle adapter includes a sealing ring formed along its outer surface, wherein the sealing ring contacts the inner wall of the filling station to form a gas-tight seal with the inner wall as the bottle adapter is inserted into the filling station.

14. The filling system of claim 13 wherein the indexing grooves of the filler spout contact and receive the indexing ridges of the keyed section prior to the sealing ring contacting the inner wall of the filling station as the bottle adapter is inserted into the filling station.

15. The filling system of claim 10 wherein each of the indexing grooves is recessed into the outer wall of the filler spout, each indexing groove being defined by a top edge, the top edge of the indexing groove being positioned below the top edge of the outer wall of the filler spout.

16. The filling system of claim 10 wherein the filler spout includes a front universal, prominent indexing groove and an agent-specific indexing groove, the width of the front indexing groove being greater than the width of the agent-specific indexing groove.

17. The filling system of claim 10 wherein the keyed section includes a front universal, prominent indexing ridge and an agent-specific indexing ridge, the width of the front indexing ridge being greater than the width of the agent-specific indexing ridge.

18. A filling system for the delivery of a liquid anesthetic agent from an anesthetic bottle to an internal sump of an anesthetic vaporizer, the system comprising:
a bottle adapter configured for attachment to the anesthetic bottle, the bottle adapter having an outlet opening through which anesthetic agent from the anesthetic bottle can be discharged;
an adapter valve assembly positioned in the bottle adapter and movable between an open position and a closed position, the adapter valve assembly including a valve head that prevents the flow of the anesthetic agent through the outlet opening when the adapter valve assembly is in the closed position;
a filling station positioned on the anesthetic vaporizer for receiving the bottle adapter and through which the anesthetic agent can flow into the internal sump of the anesthetic vaporizer; and
a filler valve assembly positioned in the filling station and movable between an open position and a closed position, the filler valve assembly including a stationary activation rod configured to contact the valve head of the adapter valve assembly and move the adapter valve assembly to the open position as the bottle adapter is inserted into the filling station and a valve body movable within the filling station, the valve body being biased into a closed position to prevent the flow of anesthetic agent into the vaporizer, wherein the bottle adapter contacts the valve body and moves the valve body to the open position as the bottle adapter is inserted into the filling station,
wherein the adapter valve assembly and the filler valve assembly are positioned such that the filling valve assembly opens prior to opening of the adapter valve assembly as the bottle adapter is inserted into the filling station.

19. The filling system of claim 18 wherein the filling station includes a cylindrical open interior defined by an inner wall and the bottle adapter includes a sealing ring formed along its outer surface, wherein the sealing ring contacts the inner wall of the filling station to form a gas-tight seal with the inner wall as the bottle adapter is inserted into the filling station.

20. The filling system of claim 19 wherein the sealing ring contacts the inner wall of the filling station prior to the bottle adapter opening the filler valve assembly to prevent the release of vapor pressure from the anesthetic vaporizer when the filler valve assembly opens.

21. The filling system of claim 18 wherein the filling station includes a cylindrical open interior sized to receive the bottle adapter, the activation rod being centered within the cylindrical open interior.

22. The filling system of claim 21 wherein the activation rod is securely mounted to a mounting block extending across and mounted to the open interior of the filling station, the mounting block having a plurality of flow openings extending therethrough, the flow openings allowing the anesthetic agent to flow through the mounting block.

23. The filling system of claim 22 wherein the valve body of the filler valve assembly includes a plurality of projecting legs that contact a top lip of the bottle adapter as the bottle adapter is inserted into the filling station, the projecting legs extending through the flow openings of the mounting block.

24. The filling system of claim 23 wherein the distance from a top end of the activating rod to a top edge of the projecting legs is less than the distance from the top lip of the bottle adapter to a face surface of the valve head, wherein the top lip of the bottle adapter contacts the projecting legs prior to contact between the activation rod and the valve head as the bottle adapter is inserted into the filling station.

25. The filling system of claim 18 further comprising:
    a cylindrical keyed section formed on the bottle adapter having at least a pair of protruding indexing ridges positioned at a first angle relative to each other around the outer circumference of the keyed section; and
    a filler spout formed on the filling station, the filler spout having a cylindrical outer wall including at least a pair of recessed indexing grooves positioned at a second angle relative to each other, wherein the indexing grooves receive the indexing ridges and allow the bottle adapter to be inserted into the filling station only when the first angle is equal to the second angle.

26. The filling system of claim 25 wherein the first angle between the indexing ridges and the second angle between the indexing grooves are determined by the type of anesthetic agent such that the filler spout can receive only one type of anesthetic agent.

27. The filling system of claim 26 wherein the indexing grooves of the filler spout contact and receive the indexing ridges of the keyed section prior to the filler valve assembly opening as the bottle adapter is inserted into the filling station.

28. The filling system of claim 25 wherein the filling station includes a cylindrical open interior defined by an inner wall and the bottle adapter includes a sealing ring formed along its outer surface, wherein the sealing ring contacts the inner wall of the filling station to form a gas-tight seal with the inner wall as the bottle adapter is inserted into the filling station.

29. The filling system of claim 28 wherein the indexing grooves of the filler spout contact and receive the indexing ridges of the keyed section prior to the sealing ring contacting the inner wall of the filling station as the bottle adapter is inserted into the filling station.

30. The filling system of claim 25 wherein each of the indexing grooves is recessed into the outer wall of the filler spout, each indexing groove being defined by a top edge, the top edge of the indexing groove being positioned below the top edge of the outer wall of the filler spout.

31. The filling system of claim 25 wherein the filler spout includes a front universal, prominent indexing groove and an agent-specific indexing groove, the width of the front indexing groove being greater than the width of the agent-specific indexing groove.

32. The filling system of claim 25 wherein the keyed section includes a front universal, prominent indexing ridge and an agent-specific indexing ridge, the width of the front indexing ridge being greater than the width of the agent-specific indexing ridge.

33. The filling system of claim 18 wherein the valve head of the adapter valve assembly is spring biased into the closed position.

34. A filling system for the delivery of a liquid anesthetic agent from an anesthetic bottle to an anesthetic vaporizer, the system comprising:
    a bottle adapter configured for attachment to the anesthetic bottle, the bottle adapter having an outlet opening through which anesthetic agent from the anesthetic bottle can be discharged;
    an adapter valve assembly positioned in the bottle adapter and movable between an open position and a closed position, wherein anesthetic agent can flow through the outlet opening when the adapter valve assembly is in the open position;
    a cylindrical keyed section formed on the bottle adapter, the keyed section having at least a pair of protruding indexing ridges positioned at a first angle relative to each other around the outer circumference of the keyed section;
    a filling station positioned on the vaporizer for receiving the bottle adapter and through which the anesthetic agent can be dispensed into an internal sump of the anesthetic vaporizer;
    a filler valve assembly positioned in the filling station and movable between an open position and a closed position, the filler valve assembly being movable to the open position upon contact with the bottle adapter as the bottle adapter is inserted into the filling station and wherein the adapter valve assembly is movable to the open position upon contact with the filler valve assembly as the bottle adapter is inserted into the filling station; and
    a filler spout formed on the filling station, the filler spout having a cylindrical outer wall including at least a pair of recessed indexing grooves positioned at a second angle relative to each other, wherein the indexing grooves receive the indexing ridges as the bottle adapter is inserted into the filling station when the first angle is equal to the second angle.

35. The filling system of claim 34 wherein the first angle between the indexing ridges is based on the type of anesthetic agent in the anesthetic bottle to which the bottle adapter is attached and the second angle between the indexing grooves is determined by the type of anesthetic agent to be received in the anesthetic vaporizer such that the filler spout can receive only one type of anesthetic agent.

36. The filling system of claim 35 wherein the indexing grooves of the filler spout receive the indexing ridges of the keyed section prior to opening of the filler valve assembly and the adapter valve assembly as the bottle adapter is inserted into the filling station.

37. The filling system of claim 34 wherein each of the indexing grooves is recessed into the outer wall of the filler spout and is defined by a top edge, the top edge of each indexing groove being positioned beneath a top edge of the outer wall defining the filler spout.

38. The filling system of claim 34 wherein the keyed section includes a front indexing ridge and an agent-specific indexing ridge, wherein the width of the front indexing ridge is greater than the width of the agent-specific indexing ridge.

39. The filling system of claim 34 wherein the filling station includes a cylindrical open interior defined by an inner wall, the bottle adapter including a sealing ring that contacts the inner wall of the filling station to form a gas-tight seal as the bottle adapter is inserted onto the filling station.

40. The filling system of claim 39 wherein the indexing grooves of the filler spout contact and receive the indexing ridges of the keyed section prior to the sealing ring contacting the inner wall of the filling station as the bottle adapter is inserted into the filling station.

41. The filling system of claim 39 wherein the sealing ring contacts the inner wall of the filling station prior to the bottle adapter opening the filler valve assembly.

42. The filling system of claim 34 wherein the filler valve assembly includes a stationary activation rod configured to contact a valve head of the adapter valve assembly to open the adapter valve assembly as the bottle adapter is inserted into the filling station and a valve body movable along the activation rod, the valve body being biased into a closed position to prevent the flow of anesthetic agent into the vaporizer, the valve body being configured to contact the bottle adapter such that the bottle adapter moves the valve body to an open position as the bottle adapter is inserted into the filling station, wherein the adapter valve assembly and the filler valve assembly are positioned such that the filler valve assembly opens prior to opening of the adapter valve assembly as the bottle adapter is inserted into the filling station.

43. The filling system of claim 42 wherein the filling station includes a cylindrical open interior sized to receive the bottle adapter, the activation rod being centered within the open interior.

44. The filling system of claim 43 wherein the activation rod is securely mounted to a mounting block positioned within the open interior, the mounting block having a plurality of flow openings that allow the anesthetic agent to flow through the mounting block.

45. The filling system of claim 44 wherein the valve body of the filler valve assembly includes a plurality of projecting legs that contact the bottle adapter as the bottle adapter is inserted into the filling station, wherein the projecting legs through the flow openings of the mounting block.

46. The filling system of claim 45 wherein the distance from a top end of the activation rod to a top edge of the projecting legs is less than the distance from a top lip of the bottle adapter to an outer face surface of the valve head such that the top lip of the bottle adapter contacts the projecting legs prior to contact between the activation rod and the valve head as the bottle adapter is inserted into the filling station.

* * * * *

UNITED STATES PATENT AND TRADEMARK OFFICE
CERTIFICATE OF CORRECTION

PATENT NO. : 6,585,016 B1
DATED : July 1, 2003
INVENTOR(S) : John C. Falligant et al.

It is certified that error appears in the above-identified patent and that said Letters Patent is hereby corrected as shown below:

<u>Title page,</u>
Item [75], the listing of inventors should be:
-- John C. Falligant, Edgerton, WI (US);
Gordon G. Sansom, Sun Prairie, WI (US)
Mark A. Thom, Madison, WI (US) --

Signed and Sealed this

Seventh Day of October, 2003

JAMES E. ROGAN
*Director of the United States Patent and Trademark Office*